(12) United States Patent
Mazzoleni et al.

(10) Patent No.: US 11,571,144 B2
(45) Date of Patent: Feb. 7, 2023

(54) SYSTEM AND METHOD FOR ESTIMATING CARDIORESPIRATORY FITNESS

(71) Applicant: Under Armour, Inc., Baltimore, MD (US)

(72) Inventors: Michael Mazzoleni, Baltimore, MD (US); Jeffrey Allen, Baltimore, MD (US); F. Grant Kovach, Baltimore, MD (US); Jeffrey Knight, Baltimore, MD (US); Matthew Trexler, Baltimore, MD (US)

(73) Assignee: Under Armour, Inc., Baltimore, MD (US)

( * ) Notice: Subject to any disclaimer, the term of this patent is extended or adjusted under 35 U.S.C. 154(b) by 1184 days.

(21) Appl. No.: 16/129,006

(22) Filed: Sep. 12, 2018

(65) Prior Publication Data

US 2020/0077927 A1    Mar. 12, 2020

(51) Int. Cl.
| A61B 5/11 | (2006.01) |
| A61B 5/00 | (2006.01) |
| A63B 24/00 | (2006.01) |
| A61B 5/22 | (2006.01) |
| A61B 5/0205 | (2006.01) |

(52) U.S. Cl.
CPC .......... *A61B 5/1118* (2013.01); *A61B 5/1112* (2013.01); *A61B 5/6831* (2013.01); *A63B 24/0062* (2013.01); *A61B 5/0205* (2013.01); *A61B 5/1123* (2013.01); *A61B 5/222* (2013.01); *A61B 5/681* (2013.01); *A61B 5/6807* (2013.01);
(Continued)

(58) Field of Classification Search
CPC ... A61B 5/1118; A61B 5/0205; A61B 5/0833; A63B 2024/0065; A63B 24/0062; G16H 50/30
See application file for complete search history.

(56) References Cited

U.S. PATENT DOCUMENTS

| 6,241,684 B1 * | 6/2001 | Amano ................ A61B 5/1118 600/529 |
| 9,237,868 B2 | 1/2016 | Seppanen et al. |

(Continued)

OTHER PUBLICATIONS

Bradshaw, Danielle I.; An Accurate VO2max Non-exercise Regression Model for 18 to 65 Year Old Adults; BYU Scholars Archive, All Theses and Dissertations, Paper 1144; Dec. 19, 2003; 58 Pages; Brigham Young University.

*Primary Examiner* — Michael J Dalbo
(74) *Attorney, Agent, or Firm* — Maginot, Moore & Beck LLP

(57) ABSTRACT

A method of determining a CRF level for a user of a fitness tracking system includes receiving activity data from at least one activity sensor carried by the user during a number of workouts, the activity data including distance data for each of the number of workouts, and then generating workout data based on the activity data. The method further includes storing the workout data in a memory, the memory further including demographic data for the user. When the an attribute of the workout data is less than a threshold number, the method includes determining a first CRF level for the user based on a first CRF model. When the attribute of the workout data is greater than the threshold number, the method includes determining a second CRF level for the user based on a second CRF model, and displaying the first and second CRF levels.

20 Claims, 8 Drawing Sheets

(52) U.S. Cl.
CPC ............... *A61B 2562/0219* (2013.01); *A63B 2024/0065* (2013.01); *A63B 2225/50* (2013.01)

(56) References Cited

U.S. PATENT DOCUMENTS

| | | | |
|---|---|---|---|
| 2015/0087929 A1* | 3/2015 | Rapoport | A61B 5/1112 600/301 |
| 2016/0206248 A1* | 7/2016 | Sartor | A61B 5/7264 |
| 2018/0174685 A1* | 6/2018 | Hämäläinen | A61B 5/02438 |

* cited by examiner

SYSTEM AND METHOD FOR ESTIMATING CARDIORESPIRATORY FITNESS

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD

The methods and systems disclosed in this document relate to the field of fitness tracking systems for monitoring user activity and, in particular, to determining a cardiorespiratory fitness level associated with a user of a fitness tracking system.

BACKGROUND

Active individuals, such as walkers, runners, and other athletes commonly use fitness tracking systems to track exercise metrics such as average speed and distance traversed during an exercise session. These individuals are typically interested in improving athletic performance over time, including increased aerobic endurance, cardiovascular health, and/or overall fitness.

Cardiorespiratory fitness (CRF) is one tool often used to measure aerobic endurance, cardiovascular health and overall fitness. CRF refers to the ability of the circulatory and respiratory systems to supply oxygen to skeletal muscles during sustained physical activity. A typical standard for measuring CRF is $VO_2$ max (also referred to herein as "VO2 max"). VO2 max is the measurement of the maximum amount of oxygen that an individual can utilize during intense, or maximal exercise (i.e., "maximum oxygen uptake"). VO2 max is typically measured as milliliters of oxygen used in one minute per kilogram of body weight (ml/kg/min).

VO2 max is difficult to measure without specialized equipment. Accurate measurements of VO2 max are typically taken in a sports performance lab using ergometers, oxygen and carbon dioxide analyzers, heart rate monitors, timers, and/or other equipment. In collecting data for a typical measurement, a high-intensity effort is performed on a treadmill or bicycle under a strict protocol. These protocols involve specific increases in the speed and intensity of the exercise and collection and measurement of the volume and oxygen concentration of inhaled and exhaled air. Data collected is inserted into an equation and a score is calculated.

Unfortunately, the need for specialized equipment prevents many athletes from knowing their CRF fitness score/level. Even if an athlete obtains a CRF fitness score at one time, there is no way for the athlete to know if his or her CRF fitness score is improving without returning to the performance lab and undergoing another CRF fitness analysis. In order to improve the user experience of fitness tracking systems, it would be desirable to provide users with an accurate estimation of current CRF fitness level without the need to repeatedly return to the performance lab. Accordingly, improvements in fitness tracking systems are desirable.

SUMMARY

In at least one embodiment, a method of operating a fitness tracking system includes receiving first activity data from at least one activity sensor carried by a user during a first number of workouts performed by the user within a period of time. First workout data is generated from the first activity data, and the first workout data is stored in a memory along with demographic data for the user. The method further comprises selecting a first model from a plurality of models for determining a cardiorespiratory fitness (CRF) level based at least in part on the first number of workouts, determining a first CRF level for the user based on the selected first model, and determining a first confidence rating for the first CRF level based at least in part on the first number of workouts. Thereafter, the first CRF level and the first confidence rating are displayed on a personal electronic device associated with the user. Additionally, the method comprises receiving second activity data from the at least one activity sensor carried by the user for a second number of workouts performed by the user over the period of time. Second workout data is generated from the second activity data, and stored in the memory. The method further comprises selecting a second model from the plurality of models for calculating a CRF level based at least in part on the first number of workouts and the second number of workouts, determining a second CRF level for the user based on the selected second model, the second model configured to determining the second CRF level based at least in part on the first workout data and the second workout data, and determining a second confidence rating for the second CRF level based at least in part on the first number of workouts and the second number of workouts. Thereafter, the second CRF level and an associated second confidence rating are displayed on the personal electronic device associated with the user.

In another embodiment, a method of determining a CRF level for a user of a fitness tracking system includes receiving activity data from at least one activity sensor carried by the user during a number of workouts performed by the user within a period of time, and then generating workout data based on the activity data, the workout data including a plurality of workout attributes and associated values. The method further includes storing the workout data in a memory, the memory further including demographic data for the user. When the value of a workout attribute is less than a threshold value, the method includes selecting a first CRF model, determining a first CRF level for the user using the first CRF model, and displaying the first CRF level on a personal electronic device associated with the user. When the value of the workout attribute is greater than the threshold value, the method includes selecting a second CRF model, determining a second CRF level for the user using the second CRF model, and displaying the second CRF level on the personal electronic device associated with the user.

In yet another embodiment, a method of determining a CRF level for a user of a fitness tracking system includes receiving activity data from at least one activity sensor carried by the user during a number of workouts performed by the user within a period of time, and then generating workout data based on the activity data, the workout data including distance data and speed/pace data for each of the number of workouts. The method further includes storing the workout data in a memory, the memory further including demographic data for the user, determining a CRF level for the user based on the demographic data, the distance data, and the speed/pace data, and determining a confidence rating for the CRF level, the confidence rating based at least in part on the number of workouts performed by the user within the period of time. The CRF level and the confidence rating are displayed on a personal electronic device associated with the user, with the CRF level being displayed as a maximum oxygen uptake score.

These and other aspects shall become apparent when considered in light of the disclosure provided herein.

BRIEF DESCRIPTION OF THE FIGURES

The foregoing aspects and other features of a fitness tracking system are explained in the following description, taken in connection with the accompanying drawings.

Figure 1:
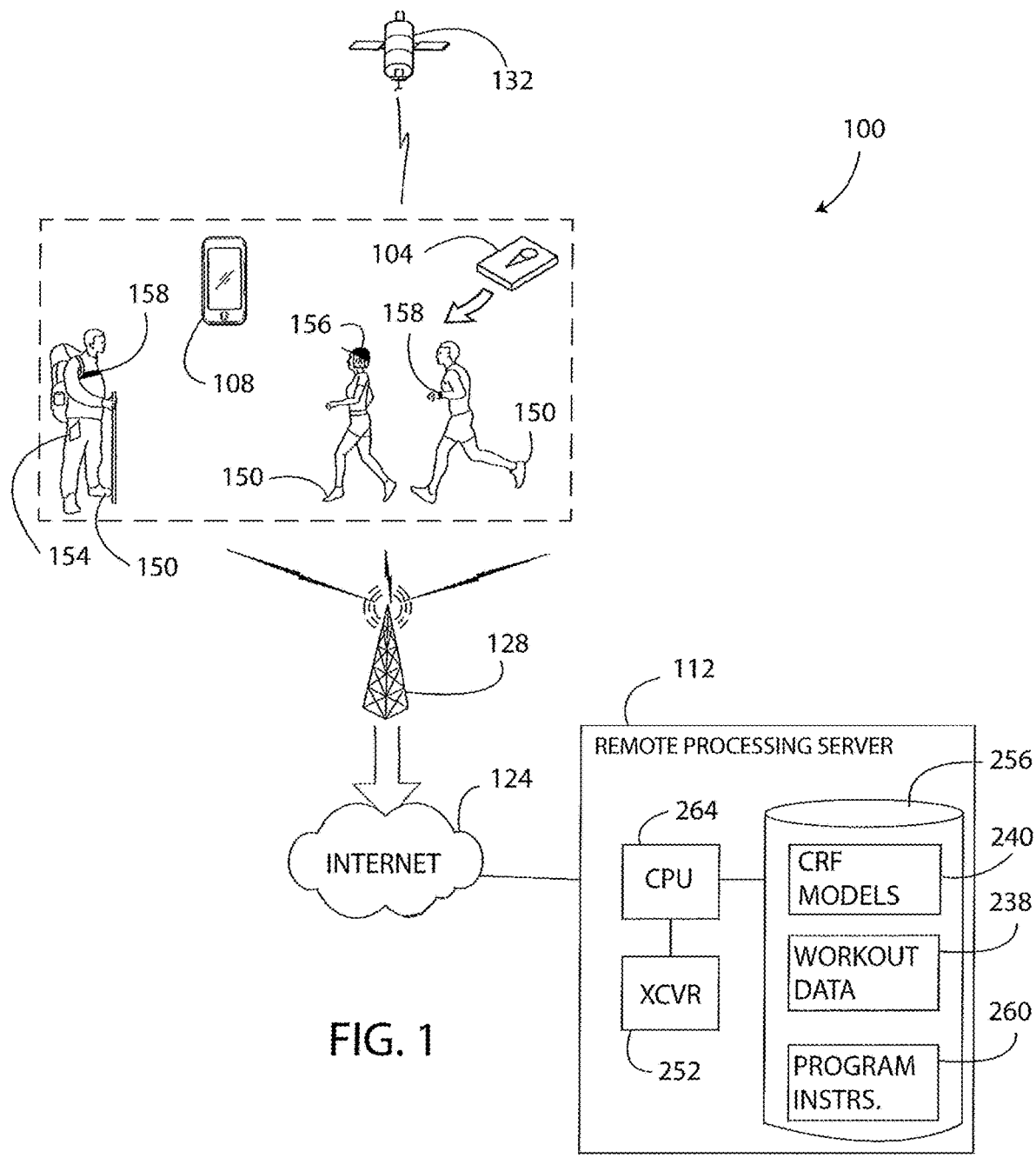
FIG. 1 is a diagram illustrating a fitness tracking system, as disclosed herein.

All Figures © Under Armour, Inc. 2018. All rights reserved.

DETAILED DESCRIPTION

Disclosed embodiments include systems, apparatus, methods, and storage medium associated for generating activity data corresponding to a movement of a user, and, in response thereto, selecting one of a plurality of CRF models based on the activity data, and determining one or more CRF levels for the user based on the selected models.

For the purpose of promoting an understanding of the principles of the disclosure, reference will now be made to the embodiments illustrated in the drawings and described in the following written specification. It is understood that no limitation to the scope of the disclosure is thereby intended. It is further understood that this disclosure includes any alterations and modifications to the illustrated embodiments and includes further applications of the principles of the disclosure as would normally occur to one skilled in the art to which this disclosure pertains.

In the following detailed description, reference is made to the accompanying drawings which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that any discussion herein regarding "one embodiment," "an embodiment," "an exemplary embodiment," and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, operations described may be performed in a different order than the described embodiments. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

Fitness Tracking System

As shown in FIG. 1, a fitness tracking system 100 includes a monitoring device 104, a personal electronic device 108, and a remote processing server 112. As disclosed herein, the fitness tracking system 100 collects activity data 136 (see FIG. 2) with the monitoring device 104 while the user performs a workout or otherwise exercises. At least one of the monitoring device 104 and the personal electronic device 108 generates workout data 238 (see FIG. 3) based on the activity data 136 collected by the monitoring device 104. The fitness tracking system 100 transmits and receives data over the Internet 124 using a cellular network 128, for example. The fitness tracking system 100 may also be configured for use with a global positioning system ("GPS") 132 and one or more GPS devices. Each component of the fitness tracking system 100 and method for operating the fitness tracking system 100 are described herein.

The monitoring device 104 is configured to be worn or carried by a user of the fitness tracking system 100. The monitoring device 104 may be provided in any number of different forms and configurations. In one embodiment, the monitoring device 104 is permanently embedded in the sole of a shoe 150 worn by the user. The monitoring device 104 may alternatively be configured for placement in the shoe 150, may be attached to the shoe 150, may be carried in a pocket 154 of the user's clothing, may be attached to a hat 156 worn by the user, and/or may be attached to any portion of the user or the user's clothing or accessories (e.g., wrist band, eyeglasses, necklace, visor, etc.). Moreover, in some embodiments, multiple monitoring devices may be used to collect activity data, such as a monitoring device in a shoe and a monitoring device on a watch, or a left monitoring device 104 located and/or affixed to the user's left shoe 150 and a right monitoring device 104 located and/or affixed to the user's right shoe 150.

In some embodiments, the monitoring device 104 includes a strap 158 to mount the monitoring device 104 onto the user. In this embodiment, the monitoring device 104 may be strapped to the user's wrist, arm, ankle, or chest, for example. In at least one embodiment, the strap 158 and the monitoring device 104 are provided as a watch or a watch-like electronic device. In a further embodiment, the monitoring device 104 is included in a heartrate monitoring device (not shown) that is worn around the wrist, chest, or other body location that is typically used to measure heartrate. Thus, the monitoring device 104 is configured for mounting (permanently or removably) on any element of the user or the user's clothing, footwear, or other article of apparel using any of various mounting means such as adhesives, stitching, pockets, or any of various other mounting means.

The monitoring device 104 is located proximate to and carried by the user during workouts and other activities such as hiking, running, jogging, walking, and the like. The personal electronic device 108 may also be carried by the user during workouts and other activities. Alternatively, because the personal electronic device 108 is separate from the monitoring device, the personal electronic device 108 may alternatively be left behind or remote from the user during such workouts and other activities. If the personal electronic device 108 is carried by the user along with the monitoring device 104, data from the monitoring device 104 may be periodically sent to the personal electronic device 108 during workouts and other activities. On the other hand, if the personal electronic device 108 is not carried by the user during a workout, data from the monitoring device 104 may be uploaded to the personal electronic device 108 at the end of a workout when the two devices are in sufficiently close proximity for communication.

Although the monitoring device 104 and the personal electronic device 108 are described generally herein as completely separate devices, each with its own processor and housing, it will be recognized that in at least some embodiments, the monitoring device 104 may be part of the personal electronic device 108. In such embodiments, the components of the monitoring device 104 are commonly housed with the personal electronic device 108, and certain components may be shared, such as a shared processor.

Figure 2:
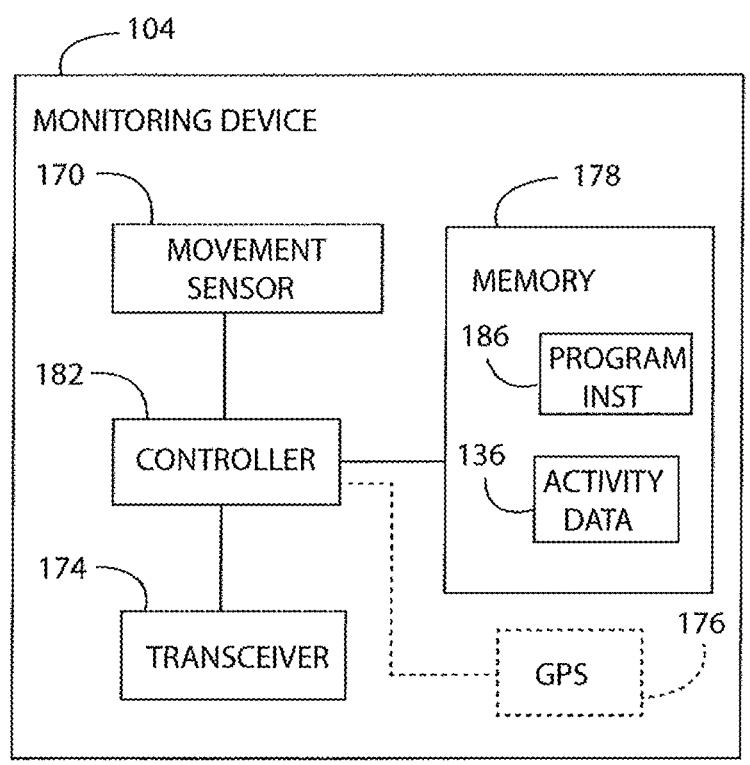
FIG. 2 is a diagram illustrating a monitoring device of the fitness tracking system of FIG. 1.

With reference now to FIG. 2, the monitoring device 104 (which may also be referred to herein as a "sensor device" or "measuring device") includes a movement sensor 170 (which may also be referred to herein as an "activity sensor"), a transceiver 174, and a memory 178 each of which is operably connected to a controller 182. The movement sensor 170 is configured to collect activity data 136, which corresponds to movement of the user during an exercise session. In one embodiment, the movement sensor 170 is an accelerometer sensor (such as a MEMS accelerometer) and the activity data 136 is (or includes) acceleration data, which corresponds to acceleration of the user during the exercise session. In this embodiment, the movement sensor 170 collects acceleration data that corresponds to bipedal movement of the user. The activity data 136 is stored by the controller 182 in the memory 178. The movement sensor 170 is provided as any type of sensor configured to generate the activity data 136, such as a single-axis or a multi-axis microelectromechanical (MEMS) accelerometer, a gyroscope, and/or a magnetometer.

The transceiver 174 of the monitoring device 104, which is also referred to as a wireless transmitter and/or receiver, is configured to transmit and to receive data from the personal electronic device 108. In one embodiment, the transceiver 174 is configured for operation according to the Bluetooth® wireless data transmission standard. In other embodiments, the transceiver 174 comprises any desired transceiver configured to wirelessly transmit and receive data using a protocol including, but not limited to, Near Field Communication ("NFC"), IEEE 802.11, Global System for Mobiles ("GSM"), and Code Division Multiple Access ("CDMA").

The memory 178 of the monitoring device 104 is an electronic data storage unit, which is also referred to herein as a non-transient computer readable medium. The memory 178 is configured to store the program instruction data 186 and the activity data 136 generated by the movement sensor 170. The program instruction data 186 includes computer executable instructions for operating the monitoring device 104. The activity data may be stored in the memory along with any other electronic data associated with the fitness tracking system 100, such as user profile information, for example, or if the workout data is generated by the monitoring device 104, the workout data.

The controller 182 of the monitoring device 104 is configured to execute the program instruction data 186 for controlling the movement sensor 170, the transceiver 174, and the memory 178. The controller 182 is a provided as a microprocessor, a processor, or any other type of electronic control chip.

In at least one embodiment, the monitoring device 104 is equipped with a GPS receiver 176. The GPS receiver 176 of the monitoring device 104 is configured to receive GPS signals from satellites of the GPS 132 (see FIG. 1). The GPS receiver 176 is further configured to generate location data that is representative of a current location on the Earth of the monitoring device 104 based on the received GPS signals. The location data, in one embodiment, includes latitude and longitude information. The controller 182 is configured to store the location data generated by the GPS receiver 176 in the memory 178 along with the activity data.

Figure 3:
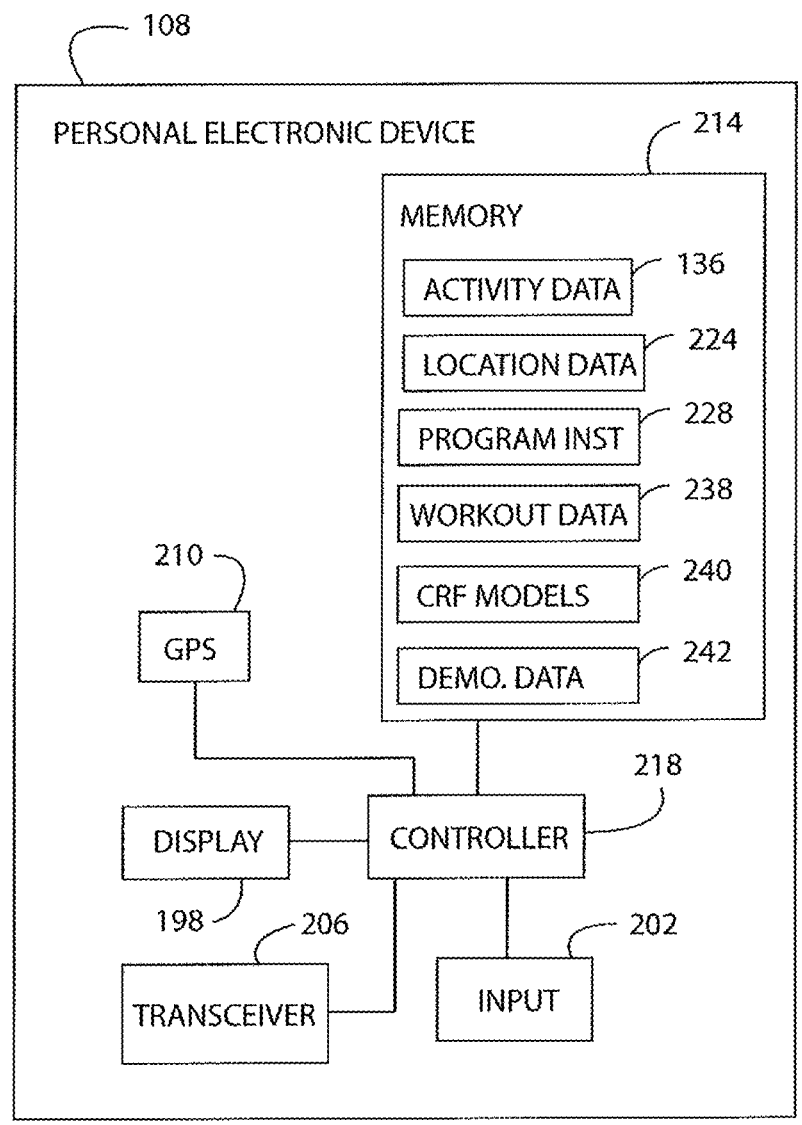
FIG. 3 is a diagram illustrating a personal electronic device of the fitness tracking system of FIG. 1.

With reference to FIG. 3, the exemplary personal electronic device 108 is configured as a smartphone. In other embodiments, the personal electronic device 108 is provided as a smartwatch, an electronic wristband, a tablet computer, a desktop computer, or the like. In one embodiment, the personal electronic device 108 is configured to be worn or carried by the user during collection of the activity data 136 by the monitoring device 104. In another embodiment, the personal electronic device 108 is not carried or worn by the user during collection of the activity data 136, and the personal electronic device 108 receives the activity data 136 from the monitoring device 104 after the user completes an exercise session. In a further embodiment, data may be transmitted from the monitoring device 104 to the personal electronic device 108 both during and after completion of an exercise session.

The personal electronic device 108 includes display 198, an input unit 202, a transceiver 206, a GPS receiver 210, and a memory 214 each of which is operably connected to a processor or a controller 218. The display 198 may comprise a liquid crystal display (LCD) panel configured to display static and dynamic text, images, and other visually comprehensible data. For example, the display 198 is configurable to display one or more interactive interfaces or display screens to the user including a display of at least an estimated distance traversed by the user, a display of an estimated speed of the user, and a display of an estimated stride length of the user. The display 198, in another embodiment, is any display as desired by those of ordinary skill in the art.

The input unit 202 of the personal electronic device 108 is configured to receive data input via manipulation by a user. The input unit 202 may be configured as a touchscreen applied to the display 198 that is configured to enable a user to input data via the touch of a finger and/or a stylus. In another embodiment, the input unit 202 comprises any device configured to receive user inputs, as may be utilized by those of ordinary skill in the art, including e.g., one or more buttons, switches, keys, and/or the like.

With continued reference to FIG. 3, the transceiver 206 of the personal electronic device 108 is configured to wirelessly communicate with the transceiver 174 of the monitoring device 104 and the remote processing server 112. The transceiver 206 wirelessly communicates with the remote processing server 112 either directly or indirectly via the cellular network 128 (FIG. 1), a wireless local area network ("Wi-Fi"), a personal area network, and/or any other wireless network over the Internet 124. Accordingly, the transceiver 206 is compatible with any desired wireless communication standard or protocol including, but not limited to, Near Field Communication ("NFC"), IEEE 802.11, Bluetooth®, Global System for Mobiles ("GSM"), and Code Division Multiple Access ("CDMA"). To this end, the transceiver 206 is configured to wirelessly transmit and receive data from the remote processing server 112, and to wirelessly transmit and receive data from the monitoring device 104.

The GPS receiver 210 of the personal electronic device 108 is configured to receive GPS signals from satellites of the GPS 132 (see FIG. 1). The GPS receiver 210 is further configured to generate location data 224 that is representative of a current location on the Earth of the personal electronic device 108 based on the received GPS signals. The location data 224, in one embodiment, includes latitude and longitude information. The controller 218 is configured to store the location data 224 generated by the GPS receiver 210 in the memory 214. The location data 224 may also be referred to herein as "GPS data."

As shown in FIG. 3, the memory 214 of the personal electronic device 108 is an electronic data storage unit, which may also be referred to herein as a non-transient computer readable medium. The memory 214 is configured to store electronic data associated with operating the personal electronic device 108 and the monitoring device 104, including program instruction data 228, activity data 136, workout data 238, CRF model data 240, and demographic data 242. The program instruction data 228 includes computer executable instructions for controlling the personal electronic device. For example, the program instructions may include computer executable instructions for generating the workout data 238 based on the activity data 136 received from the monitoring device 104.

The activity data 136 is the data received from the monitoring device 104 or otherwise input by the user. The workout data 238 includes data related to each workout performed by the user when carrying the monitoring device 104. As noted previously, the workout data 238 is automatically generated based on the activity data 136. The workout data 238 includes a number of different workout attributes that define the workout and associated values. For example, the workout attributes may include type of workout, time, distance traversed, speed, pace, cadence, heart rate, stride length, ground contact time, ground contact time percentage, foot strike pattern, efficiency, movement quality, fatigue index, power output, or any of various additional workout attributes and values, including cumulative values, average values (such as mean, median or mode), instantaneous or split-time values within the workout for any of such attributes. As described in further detail below, in at least one embodiment the workout attributes will at least include distance data and speed and/or pace data for each workout, particularly when the workout is a walk or a run. (Because speed and pace are related calculations that may be derived from one another, i.e., speed is distance/unit time and pace is time/unit distance, speed data and pace data may be referred to in the alternative herein as "speed/pace data."). Distance and speed/pace data for may be calculated based on the GPS data and/or the activity data using any of various known methods, as will be recognized by those of ordinary skill in the art. While the workout data has been described herein as being automatically generated based on the activity data, in at least one embodiment at least some of the workout data may be input manually by the user. For example, if a user conducted a workout and failed to wear the monitoring device 104, the user may be allowed to manually input workout data (e.g. time duration, distance, pace, activity type, etc.).

In addition to data for a single workout, the workout data 238 may further include cumulative workout data for a group of workouts performed over a period of time. For example, the workout data 238 may include a total or an average attribute value for a group of run-type workouts performed within the past week or month. Exemplary cumulative workout data includes a total distance traversed over a period of time, an average distance per workout, an average speed/pace for the group of workouts, etc. The above-referenced attributes are exemplary, and the controller 218 and/or the controller 182 may be configured to perform any of various calculations using the activity data 136 and/or the workout data 238 in order to arrive at the cumulative workout data. The workout data 238 may be limited to workout data performed by the user within a given period of time (e.g., within the past year), or may include all workout data ever generated for the user on the personal electronic device 108.

The CRF model data 240 includes a number of different models for determining a CRF level of the user. As described in further detail below, each CRF model includes a set of rules that determines when the model is used based on the available workout data 238 and demographic data 242, and how the CRF level is determined based on such data. The CRF levels determined from the CRF model data 240 may be provided in different forms such as a CRF score (e.g., between 20 and 80) or a CRF category (e.g., low, medium, high).

The demographic data 242 is based on demographic information of the user and may include one or more of various demographic identifiers for the user such as gender, height, weight, body mass index ("BMI"), age, body fat percentage, resting heart rate, and other data. Any other user demographic and/or physiological data may be included in the demographic data 242. The demographic data 242 may also be referred to herein as "user profile data."

The controller 218 of the personal electronic device 108 is operatively connected to the monitoring device 104 and is configured to execute the program instruction data 228 in order to control the components of the personal electronic device 108, including the display 198, the input unit 202, the transceiver 206, the GPS receiver 210, and the memory 214. The controller 218 is provided as a microprocessor, a processor, or any other type of electronic control chip. The controller 218 is configured to process at least a subset of the activity data 136 and/or the GPS data 224 and to calculate the workout data 238 by applying at least one rule of a set of rules to the subset of the activity data 136. For example, the controller 218 may be configured to calculate speed data and distance data from a subset of the activity data 136 by integrating the subset of the activity data 136. Alternatively, the controller 218 may be configured to calculate speed data and distance data based on the GPS data 224.

With reference again to FIG. 1, the remote processing server 112 is remotely located from the monitoring device 104 and the personal electronic device 108. That is, the server 112 is located in a first physical location and the personal electric device 108 and the monitoring device 104 are located in a second physical location that is different from the first physical location. The server 112 is configured to receive and store the workout data 238 from the personal electric device 108 via the Internet 124. To this end, the server 112 includes a transceiver 252, a central processing unit ("CPU") 264, and a memory 256. Each of the transceiver 252 and the memory 256 is operably connected to the CPU 264.

The memory 256 of the remote processing server 112 includes program instructions 260, the workout data 238, and CRF models 240. The server 112 is configured to receive the activity data 136 and the workout data 238 and store backup copies of the workout data 238, and/or generate additional workout data, such as CRF levels for each user using the CRF models 240, when such CRF levels are not otherwise generated by the personal electronic device 108. Although not shown in FIG. 1, it will be recognized that the memory 256 may also include additional data, such as the demographic data 242 for the user, or a copy of other data related to the user. Accordingly, it will be recognized that the remote processing server 112 may be used as a backup storage location as well as either a primary or secondary processing location for the workout data 238. In some embodiments of the fitness tracking system 100, all of the workout data and CRF levels are generated on the personal electronic device 108 without the user of the remote processing server. In other embodiments, some or all of the workout data and CRF levels are generated on the remote processing server 112.

The transceiver 252 of the remote processing server 112 is configured to wirelessly communicate with the personal electronic device 108 either directly or indirectly via the cellular network 128, a wireless local area network ("Wi-Fi"), a personal area network, and/or any other wireless network. Accordingly, the transceiver 252 is compatible with any desired wireless communication standard or protocol including, but not limited to, Near Field Communication ("NFC"), IEEE 802.11, Bluetooth®, Global System for Mobiles ("GSM"), and Code Division Multiple Access ("CDMA").

The CPU 264 of the remote processing server 112 is configured to execute the program instruction data 260 stored in the memory 256 for generating and/or determining workout data 238, including CRF levels, by applying one or more of the CRF models 240 to the workout data 238 and/or other data available to the remote processing server. The CPU 264 is provided as a microprocessor, a processor, or any other type of electronic control chip.

Creation of CRF Models

The CRF models 240 stored on the remote processing server 112 and/or the personal electronic 108 includes a number of different regression models. Each of these regression models may be used to estimate VO2 max for a user, and thus an associated estimated CRF level for the user. Each regression model includes a number of different inputs, which may be based on demographic data, workout data, or other data. Examples of inputs that may be used by different regression models include gender, age, body mass index (BMI), average heart rate, average pace, distance traversed, a physical activity rating and/or a functional ability rating based on the workout data. Each regression model (of the CRF models 240) may be created by the owner/operator of the fitness tracking system 100 or may be obtained from one or more third party sources. The regression models may be linear (e.g., using linear regression) or non-linear (e.g., using polynomial regression or artificial neural network/machine learning regression).

One example of a regression model that may be collected from a third party is the publicly available regression model for estimating VO2 max derived by Danielle Bradshaw (see Bradshaw, Danielle I., "An Accurate VO2 max Non-exercise Regression Model for 18 to 65 Year Old Adults" (2003). *All Theses and Dissertations*. Paper 1144, hereinafter, the "Bradshaw Paper".) The Bradshaw Paper describes a regression equation to predict VO2 max based on non-exercise data. A laboratory assessment of VO2 max was performed for the participants, and data was collected for each participant including the participant's age, gender, body mass index (BMI), perceived functional ability (PFA) to walk, jog, or run given distances (based merely on the user's own subjective determination of their ability to perform different workouts), and current physical activity (PA-R) level (based on recent physical activity reported by the participant). After charting the data and performing a regression analysis, the following regression model was derived:

$$VO2\ max(mL \cdot kg^{-1} \cdot min^{-1}) = 48.0730 + (6.1779 \times gender) - (0.2463 \times age) - (0.6186 \times BMI) + (0.7115 \times PFA) + (0.6709 \times PA\text{-}R),$$

where for gender female=0 and male=1

(hereinafter, the "Bradshaw Model").

While the Bradshaw Model is one possible regression model that may be used in arriving at a VO2 max calculation, it will be recognized that numerous regression models are contemplated herein as being included in the CRF models 240. While the Bradshaw Model is based on the inputs of gender, age, BMI, PFA and PA-R, different inputs are contemplated in other models. For example, a second regression model that is related to but distinct from the Bradshaw Model uses only demographic inputs for the user such as gender, age, weight, height, etc. As another example, a third regression model uses both demographic data and workout data, but does not include any perceived or actual functional ability level (e.g., distance traversed during each workout may be used as an input, but no performance data such as pace or heart rate is used as an input). As yet another example, a fourth regression model uses both demographic data and workout data, including both workout distance data and workout performance data (e.g., pace, heart rate, or other performance data may be used as an input).

At least one exemplary regression model is a modified version of the Bradshaw Model wherein the PA-R and PFA inputs are modified based on actual workout data. In this model, the regression model is as follows:

$$VO2\ max(mL \cdot kg^{-1} \cdot min^{-1}) = 48.0730 + (6.1779 \times gender) - (0.2463 \times age) - (0.6186 \times BMI) + (0.7115 \times PFA') + (0.6709 \times PA\text{-}R'),$$

where for gender female=0 and male=1,

PFA' is a functional ability rating based on an athletic performance metric derived from the workout data, and PA-R' is a physical activity rating that is based on an amount of activity derived from the workout data.

The foregoing regression model may be referred to herein as the "Workout-Based Model." As noted above, in the Workout-Based Model, both the PA-R' input and the PFA' input are variable metrics that are derived from the user's workout data. Because both PFA' and PA-R' are determined based on workout data, these inputs may also be referred to herein as workout data or, alternatively, as workout features.

In the Workout-Based Model, PA-R' is derived based on the total distance traversed by the user during a period of time. In at least one embodiment, this total distance is derived based on the workout data (e.g., the cumulative distance traveled over a number of workouts performed by the user over the period of time). In an alternative embodiment, the total distance is based both on the workout data 238 and non-workout data (e.g., other activity data generated by a step tracker or other activity tracking device). The period of time used to determine the total distance traversed by the user may any number of different periods, such as days, weeks, months, etc. The following is an exemplary table that illustrates a rule for assigning PA-R' points to the user based on distance travelled by the user:

| Total Weekly Workout Distance | PA-R' Points |
| --- | --- |
| Less than 0.1 miles | 0 |
| 0.1 to 0.25 miles | 1 |
| 0.25 to 0.5 miles | 2 |
| 0.5 to 0.75 miles | 3 |
| 0.75 to 1 miles | 4 |
| 1 to 5 miles | 5 |
| 5 to 10 miles | 6 |
| 10 to 15 miles | 7 |
| 15-20 miles | 8 |
| 20-25 miles | 9 |
| 25-35 miles | 10 |
| 35-50 miles | 11 |
| 50-75 miles | 12 |
| More than 75 miles | 13 |

While the foregoing rule for determining PA-R' points is based exclusively on distance travelled, it will be recognized that in other embodiments other workout variables may be utilized to calculate the PA-R' points, such as total workout time for the week.

In the Workout-Based Model, PFA' is also based on the workout data 238, and particularly performance-type data. For example, PFA' may be derived based on a set of rules that determine an estimated "typical workout" for the user from the workout data 238, and an associated "typical workout pace for the user."

Figure 4:
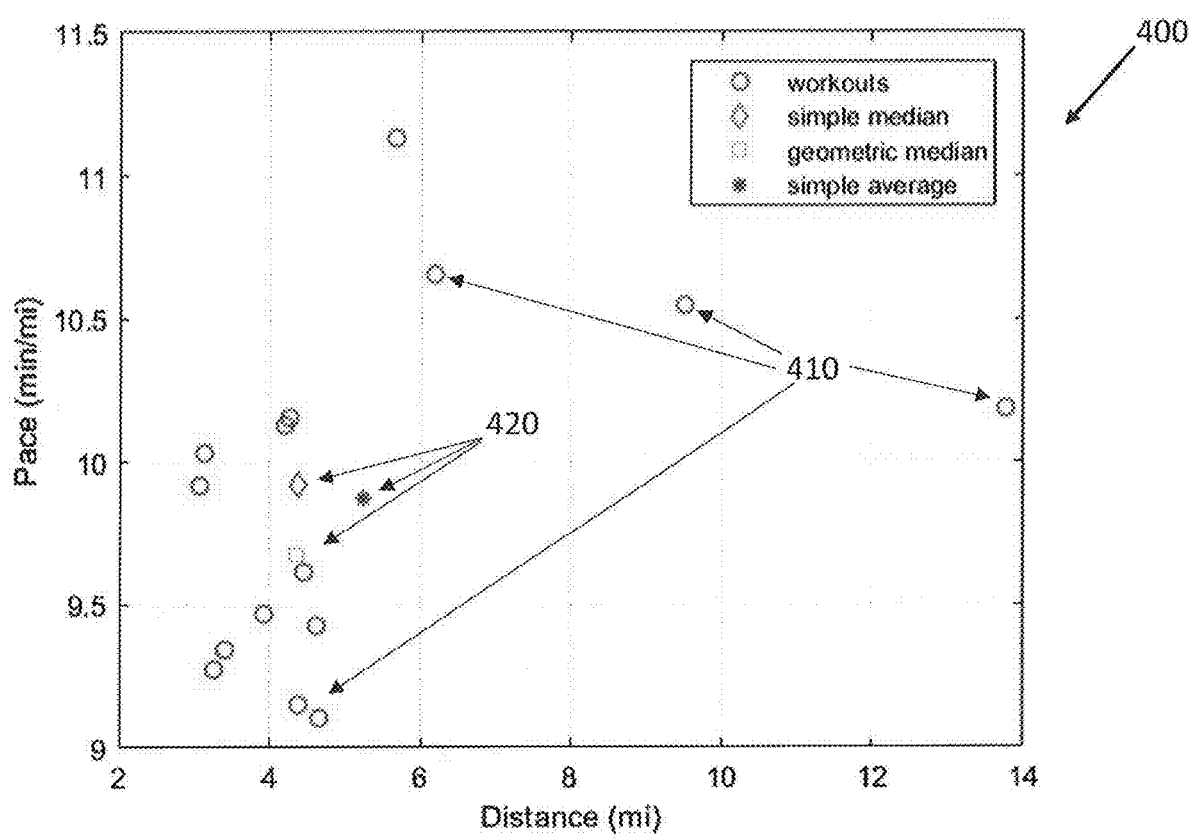
FIG. 4 is a graph illustrating workout data for a plurality of workouts performed by a user of the fitness tracking system of FIG. 1.

An example of workout data used to arrive at a typical workout for a user is shown by the graph 400 of FIG. 4. In FIG. 4, a number different workouts of a user are represented by the circles 410 of the graph 400. Each workout 410 is defined at least in part by a distance travelled during the workout (x-axis) and an average pace during the workout (y-axis). Based on the information for the workouts 410, a number of averages 420 can be calculated in order to define a typical workout for the user based on the total number of workouts. These averages 420 that define the "typical workout" may be based on any of various calculations derived from all of the workouts 4110, such as a mean, median, mode, geometric median, etc. FIG. 4 shows a simple median for the workouts 410 (represented by the diamond-shaped marker on the graph 400), a geometric median for the workouts (represented by the square-shaped marker on the graph 400), and a simple average/mean for the workouts (represented by the asterisk marker on the graph 400). Data associated with one or more of these averages 420 is then used to determine PFA' points for the user. For example, the average pace of the user during a "typical workout" may be used to arrive at the PFA' points for the user. The following is an exemplary table that illustrates a rule for assigning a PFA' points based on the average pace of the user during a typical workout:

| Average Workout Pace | PFA' Points |
| --- | --- |
| Less than 2 mph | 1 |
| 2 mph to 3 mph | 2 |
| 3 mph to 4 mph | 3 |
| 4 mph to 5 mph | 4 |
| 5 mph to 6 mph | 5 |
| 6 mph to 7 mph | 6 |
| 7 mph to 8 mph | 7 |
| 8 mph to 9 mph | 8 |
| 9 mph to 10 mph | 9 |
| 10 mph to 11 mph | 10 |
| 11 mph to 12 mph | 11 |

While the foregoing rule for determining PFA' points in the Workout-Based Model is based exclusively on average pace, it will be recognized that in other embodiments other workout variables may be utilized to calculate the PA-R' points, such as typical workout distance. In such embodiments, the PFA' points may be increased or decreased based on the typical workout distance. For example, if the typical workout distance is less than 1.5 miles, the PFA' points may be decreased by 4, or if the typical workout distance is less than 2.5 miles, the PFA' points may be decreased by 2. As another example, if the typical workout distance is greater than 7, the PFA' points may be increased by 2, and if the typical workout distance is greater than 10, PFA' points may be increased by 4.

The foregoing description of the Workout-Based Model is but one exemplary model that may be used by the fitness tracking system 100. In at least one embodiment of the fitness tracking system 100, the CRF models 240 include alternative models that may be used based on the available data for the user, including the sufficiency and availability of both workout data 238 and demographic data 242. The sufficiency of the workout data 238 can be determined based on the quantity and type of data. For example, the number of workouts logged over a specified time period must exceed a specified threshold number (e.g., ten workouts within a month), these workouts must contain at least workout distance data (i.e., a total distance traversed for all the workouts), the workout type must be for walking or running, and/or any of various other rules for determining sufficiency of workout data 238. Similarly, the sufficiency of the demographic data 242 can be determined based on the existence or non-existence of various data types. For example, the demographic data must include at least age, gender, height, weight, and/or any of various other demographic data attributes. In such an embodiment, the CRF model that is selected may be based on a tiered system of sub-models in order to account for missing data or sparse data (i.e., missing or sparse workout data 238 or demographic data 242).

A first example of a tiered sub-model is a model that is implemented when demographic data 242 is sufficiently available (i.e., a full user profile with all necessary inputs for the model is included in the demographic data 242), but workout data 238 is missing or sparse (e.g., the user has not logged any workouts or only a small number of workouts). According to this sub-model, only demographic data for the user is used to arrive at an estimated CRF level.

A second example of a tiered sub-model is a model that is implemented when workout data 238 is sufficiently available (e.g., the user has logged numerous workouts using the fitness tracking system 100 within a predetermined period of time), but demographic data is missing or sparse (e.g., one or more of age, gender, height, weight, BMI, etc. is missing). According to this sub-model, only workout data for the user is used to arrive at the estimated CRF level. An example of such a model would be the Workout-Based Model discussed above but modified to only use the PFA' and PA-R' inputs.

A third example of a group of tiered sub-models are those that are implemented when workout data 238 and demographic data 242 are both available, but some of this data is missing or sparse (e.g., an age is missing from the demographic data 242 or the user has only logged a small number of workouts). According to this sub-model, the workout data 238 and the demographic data 242 for the user are both used to arrive at the estimated CRF level, but the inputs are limited based on the availability of the data. An example of such a model would be a modified version of the Workout-Based Model discussed above wherein one or more inputs are dropped out of the model, based on the availability of data. For example, if demographic data for age is not available, the age input is removed from this model. As another example, if workout data is limited because pace data is not available (but total distance data is available), the PFA' input may be dropped out of the model, but the PA-R' input may remain in the model. According to these sub-models, inputs are dropped out based on certain types of data being unavailable (e.g., age or pace) within the workout data 238 and the demographic data 242.

In addition to the foregoing it will be recognized that various additional embodiments where data is missing or sparse, the sufficiency of available data may be based on one or more threshold values. For example, the model may be configured to only accept certain data when the user has completed a threshold number of workouts within a given period of time. As an example, assume that according to one model, a first threshold for a number of workouts within a month is seven and a second threshold for a number of workouts within a month is demographic data for a user is twelve. Also assume that a particular user has complete demographic data, and has completed ten workouts within a month. In this instance, the workout data satisfies the first sufficiency criteria (i.e., ten workouts within the month is greater than the threshold of seven), but the workout data fails the second sufficiency criteria (i.e., ten workouts within the month is less than the threshold of fifteen). In this instance the model that is used to estimate a CRF level for the user incorporates the PA-R' input, but does not incorporate the PFA' input (i.e., it is determined that the number of workouts is sufficient to provide a physical activity rating based on total distance of the user, but the number of workouts is insufficient to provide a true functional ability rating). This is but one example of a sub-model that could be used based on limited or sparse workout data 238. It will be recognized that various other input thresholds and calculations are possible depending on the linear regression models utilized by the fitness tracking system.

A fourth example of a tiered sub-model is a model that is implemented when workout data 238 and demographic data 242 are both complete and fully available. According to this sub-model, both the workout data 238 and the demographic data 242 for the user are used to arrive at the estimated CRF level. An example of such a model would be the Workout-Based Model discussed above wherein demographic data 242 and workout data 238 both satisfy some sufficiency criteria, and are fully incorporated into the model.

In addition to the existence of various different CRF models, it will be appreciated that different CRF models may be selected at different times for use in calculating a CRF level for the user. Accordingly, a number of different CRF models may be used within a single period of time in order to arrive at different CRF levels for the user. Consider a user who completes a first number of workouts within the first half of a predetermined time period (e.g., within the first fifteen days of a month), and then completes a second number of workouts within the second half of the predetermined time period (e.g., within the last fifteen days of the month). In this example, a first CRF model is selected when a CRF level is determined half-way through the month. Selection of this first CRF model is based on (i) the first number of workouts being greater than a first threshold number, and (ii) the existence of distance data for the number of workouts. According to this model, the first CRF model is selected and the first CRF level is determined based at least in part on both the demographic data of the user and the distance data for the number of user workouts. Subsequently the user performs the second number of workouts in the second half of the month, and a second CRF level for the user is determined within the month using a second CRF model. Selection of the second CRF model is based at least in part on (i) the first and second number of workouts being greater than a threshold number, (ii) an existence of distance data for the first and second number of workouts, and (iii) an existence of speed/pace data for each of the first and second number of workouts, wherein the second model determines the second CRF level based at least in part on the demographic data, the distance data, and the speed/pace data for the first and second number of workouts.

Calculation of CRF Levels

Each of the CRF models 240 are regression models that are configured to calculate an estimated CRF level for the user. The CRF models are configured to calculate a CRF level for the user as either a numerical value (e.g., between 0 and 100) or a categorical rating (e.g., "low," "medium," "high") and then transmit the estimated CRF level to the user's personal electronic device 108 for display. According to at least one embodiment, the determined CRF level for the user is simply a VO2 max score (e.g., a score between 10 and 80 ml/kg/min) that is displayed for the user on the personal electronic device 108. In other embodiments, each model is configured to calculate a VO2 max score and then translate that VO2 max score into a more descriptive CRF level, such as a CRF category or rating that is based in part on the user's demographic data such as age and gender. For example, after determining a VO2 max score, each CRF model may utilize a table to translate the determined score into a rating such as "excellent," "good," "above average," "average," "below average," "poor," or "very poor." Again, this categorical rating for the user is typically based on various demographic factors for the user, such as gender and age. However, in at least one embodiment, additional or different demographic factors may be considered when determining the user's CRF level. For example, based on the demographic information collected for the user, the user may be presented a CRF level that is based at least in part on geographic region of residence, occupation, marital status, typical workout type (e.g., runner, biker, walker), etc. In at least one embodiment, the user is provided with the opportunity to define the demographic data used to determine his or her CRF level relative to other users in of the fitness tracking system. This feature provides the user with the ability to compare himself or herself to other similarly situated individuals based on factors other than just age and gender.

As noted previously, the CRF models 240 may be embedded in a processor of a cell phone or other personal electronic device, or may be embedded in a remote server accessed via the internet. Accordingly, the calculations for determining an estimate CRF level for each user may be performed on the user's cell phone or other personal electronic device, or on a remote computer. In at least one embodiment, CRF levels are calculated in a distributed manner using both a remote computer and a personal electronic device of the user.

The determined CRF level may be presented to the user as a single summary value representing their current estimate of CRF level (e.g., as calculated based on workout data received within the past week, month, year or years) or as a time series showing their cardiorespiratory fitness estimate over time (e.g., a series of CRF levels as calculated over a past number weeks, months or years). When the CRF level is presented to the user as a time series, the user is able to quickly and easily see his or her progress toward a fitness goal over time.

Confidence Ratings

In addition to presenting an estimated CRF levels to the user (whether as a numerical value or as a categorical rating), the fitness tracking system 100 is also configured to provide the user with a confidence rating for the CRF level. This confidence rating may be a numerical value or score (e.g., a number between 1 and 10) or a categorical rating (e.g., "low," "medium," "high," etc.). The confidence score provides the user with an understanding of how accurate the estimated CRF level is for the user. When a high confidence rating is presented, the user can be confident that the associated CRF level is very close to the user's actual CRF level as would be measured in a fitness lab. When a low confidence rating is presented, the user will understand that the associated CRF level is likely to change over time as additional data for the user (e.g., additional demographic data and/or workout data) is collected by the fitness tracking system.

Confidence ratings for the estimated CRF levels calculated by the fitness tracking system 100 may be determined based on a number of different factors. In at least one embodiment, confidence ratings are based on workout sample size available for the user in the workout data 238. Accordingly, a higher confidence rating will be generated as the sample size of workouts within a given time window increases (e.g., a user with twelve workouts logged in a month will have a higher confidence rating than a user with two workouts logged within a month).

In an alternative embodiment, confidence ratings are based on a sensitivity analysis such as a leave-one-out sensitivity analysis. Accordingly, a higher confidence rating will be generated as leave-one-out variance decreases. For example, consider a situation where a time window for analysis includes workout data from ten different logged workouts. In this situation, the selected CRF model is run ten separate times to produce ten separate VO2 max estimates based on the ten unique subsets of data that each exclude the data from one of the workouts. The variance of these ten VO2 max estimates is calculated, and a higher confidence rating is associated with a lower variance (and vice-versa).

In yet another embodiment, confidence ratings are based simply on the selected CRF model such that a confidence rating is assigned based only on the CRF model used to arrive at the estimated CRF level. In this embodiment, a CRF model that uses only demographic data but no workout data will have a low confidence rating. A CRF model that uses a limited combination of demographic data and workout data based on limited availability of such data will have a medium confidence rating. A CRF model that uses a combination of demographic data and workout data in with full availability of such data will have a high confidence rating.

In at least one embodiment, the fitness tracking system provides a notification to the user in association with the displayed confidence rating, and particularly when the confidence rating is low. This notification informs the user of the reason why the confidence rating is low. For example, the notification may inform the user to "update your user profile to include your gender," or "continue logging workouts."

Figure 5:
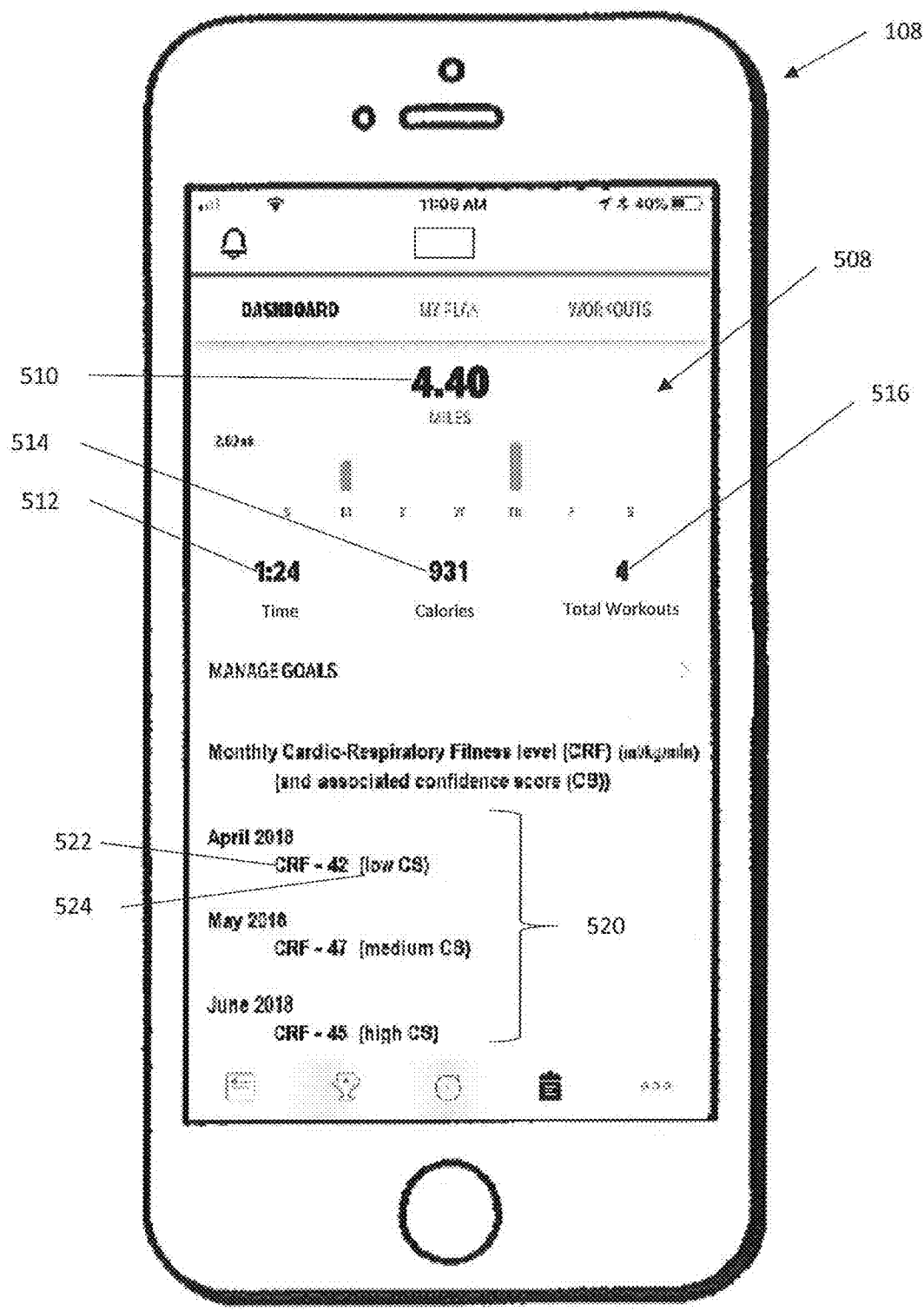
FIG. 5 shows a personal electronic device and an associated display of the fitness tracking system of FIG. 1.

FIG. 5 shows an exemplary personal electronic device 108 running a fitness tracking application as shown on a display screen 508 of the device 108. As shown in FIG. 5, the display screen 508 shows a dashboard for the user including a summary of workouts for the week. The summary includes total miles traversed 510, total workout time 512, total calories burned 514, and total number of workouts 516. Below the weekly summary is a CRF portion 520 of the display 508 that includes a number of estimated CRF levels 522, and a confidence rating 524 for each CRF level.

The CRF portion 520 of the display 508 includes a time series includes CRF levels 522 for the user in each of April, May and June of 2018. The estimated CRF level 522 for April was 42 ml/kg/min, with a confidence rating 524 (referenced on the display as a "confidence score") of "low." The estimated CRF level 522 for the user in May was 47 ml/kg/min, with a confidence rating 524 of "medium." The estimated CRF level 522 for June was 45 ml/kg/min, with a confidence rating 524 of "high." As discussed previously, the confidence ratings 524 for each of the CRF levels 522 may have been determined using any of various means. For example, the low confidence rating 524 for April could be the result of missing or sparse data (e.g., a small sample size as the result of a low number of workouts), a large variance resulting from a sensitivity analysis (even if workout data was sufficient and complete for April), or a low confidence rating associated with the CRF model used to calculate the CRF level for the month, or some combination of such factors. The "medium" and "high" confidence ratings for May and June, respectively, result from similar reasons. In any event, based on the confidence ratings for April, May and June, the user can be relatively certain that his or her VO2 max is near 45 because of the "high" confidence rating for June 2018.

In at least one embodiment, the fitness tracking system 100 provides advice, recommendations, or offers to the user based on the estimated CRF levels and the associated confidence scores. For example, if the fitness tracking system 100 detects that a particular user has a CRF level below the average CRF level for other users of the same age and gender, the fitness tracking system may provide recommendations for improving the users CRF level. As another example, if the fitness tracking system detects that a particular user has a high CRF level, the fitness tracking system may recommend that the user join a local club or other group of other high-level athletes.

In view of the foregoing, the user of the fitness tracking system 100 is provided with a device that is capable of providing CRF levels for the user over time, each of the CRF levels being associated with different confidence scores. This feature improves the fitness tracking system 100 by allowing the fitness tracking system to provide the user with accurate CRF levels without the need to visit a fitness laboratory to have his or her CRF level measured using special equipment. Such highly accurate CRF levels have heretofore been impossible to determine without the use of specialized equipment. The fitness tracking system 100 is a significant improvement over prior systems that merely estimate a CRF level based on user-perceptions or user-reported data. The devices and methods described herein improve on other fitness tracking systems by using a numerous different CRF models, selecting one of the CRF models for use based on the data available within the fitness tracking system, determining a CRF level and an associated confidence score, and then displaying the determined CRF level and confidence score to the user on his or her personal electronic device.

Method for Estimating CRF Levels

Figure 6:
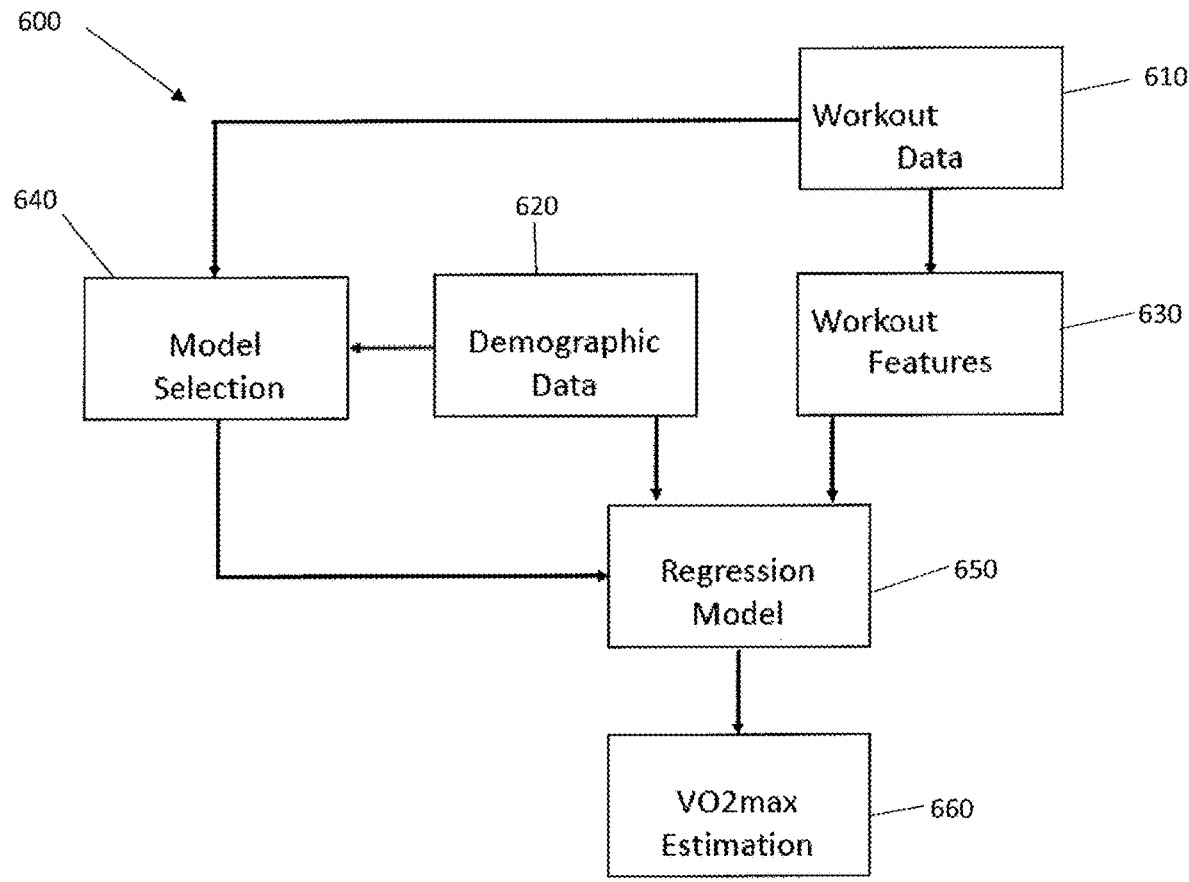
FIG. 6 is a block diagram illustrating method for determining a CRF level of a user using the fitness tracking system of FIG. 1.

With reference now to FIG. 6, a block diagram 600 is shown illustrating a method of operating the above-described fitness tracking system 100 is illustrated. As illustrated in blocks 610 and 620, both workout data 238 and demographic data 242 are used in the method. The demographic data 242 is typically entered manually by the user of the fitness tracking system, but may be obtained in other ways, such as from other applications linked to the fitness tracking system, or from third party sources. The workout data 238 is generated from activity data received from at least one activity sensor provided on a monitoring device 104 carried by the user during one or more workouts. The workout data 238 may be generated at any of various locations such as the monitoring device 104, the user's personal electronic device 108, or a remote server 112 (as shown in FIG. 1). The workout data 238 and the demographic data 242 are both stored in a memory and available for use according to the method. For example, as shown in FIG. 3, both workout data 238 and demographic data 242 are stored in the memory 214 of the user's personal electronic device 108.

As shown in block 630 of FIG. 6, workout features for the user may be determined based on the workout data. These workout features may be utilized as inputs in association with various CRF regression models. For example, the workout features may include the PFA' and PA-R' calculations used in the Workout-Based Model described previously herein. Because the workout features are derived from the workout data, these "workout features" are also considered to be part of the "workout data 238."

As shown in block 640 of FIG. 6, the method includes selecting at least one CRF model from a plurality of models for determining a CRF level. This selection is based on one or more of the available workout data 238 and demographic data 242. For example, in at least one embodiment discussed previously, the selection of a CRF model is based on a number of workouts for the user over a period of time. If the number of workouts exceeds a threshold number, one CRF model may be selected. If the number of workouts is less than the threshold number a different CRF model is selected. An example of this selection process is described in further detail below with reference to FIG. 7. In another example, the selection of CRF models is based on the availability of distance data and/or speed/pace data. An example of this selection process is described in further detail below with reference to FIG. 8.

With continued reference to FIG. 6, block 650 shows that after a CRF model (i.e., a "regression model") is selected, various inputs are inserted into the regression model. These inputs include one or more of the demographic data 242 (as shown in block 620), the workout data 238 (as shown in block 610), and the associated workout features (as shown in block 630).

As shown in block 660, after the appropriate inputs are inserted into the selected CRF model (i.e., the selected "regression model"), a VO2 max estimation is output from the model. Based on this VO2 max estimation, a CRF level is determined along with a confidence rating for the CRF level. As discussed previously, the confidence rating may be based on numerous factors. For example, the confidence rating may be based on a number of workouts for the user within the predetermined period of time. Both the determined CRF level and the confidence rating are then displayed for the first user on the personal electronic device 108.

After determination and display of a first CRF level, as described above, the method of FIG. 6 is repeated at a later time to provide a second CRF level. In particular, the method is periodically repeated in order to determine multiple updated CRF levels for the user. Each time the method is repeated, the activity tracking system selects an appropriate CRF model for use based on the available workout data 238 and demographic data 242. Each of these subsequent CRF levels is associated with a confidence rating. It will be recognized that the confidence rating for each subsequent CRF level will likely increase over time as additional workout data and/or demographic data is collected for the user and available to the fitness tracking system in determining the CRF level of the user. However, it is possible for the confidence rating for a subsequent CRF level to decrease over time. For example, confidence ratings for CRF levels may decrease when the user workouts less often, or when workout data or demographic data is lost or removed for some reason.

Figure 7:
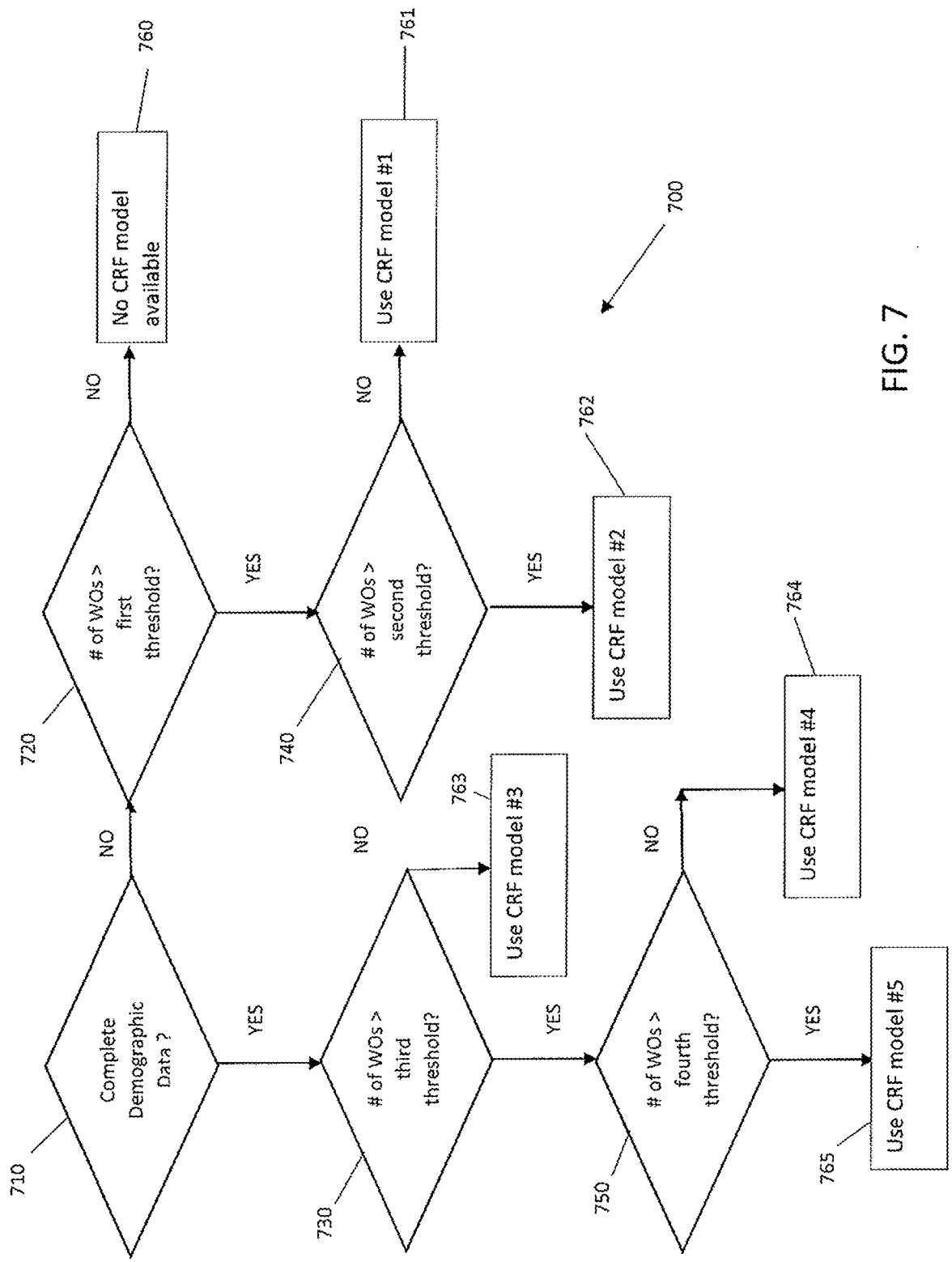
FIG. 7 is a flowchart illustrating a first method of selecting a CRF model for the method of FIG. 6.

With reference now to FIG. 7, a flowchart 700 is shown for an exemplary method for selecting a CRF model from the plurality of stored CRF models 240 (which process was referenced in block 640 of FIG. 6). The method 700 begins with step 710 where it is determined whether the sufficient demographic data for the user is available (e.g., a determination that age, gender, height and weight all exist for the user in the database/memory 214). If sufficient demographic data is not available for the user, the method moves to step 720.

At step 720, a determination is made whether the number of workouts for the user within a predetermined period of time (e.g., a month) is greater than a first threshold (e.g., zero, one, two, three workouts, etc.). If the number of workouts is not greater than the first threshold number, the method moves to step 760, and a determination is made that no CRF model is available, and no CRF level will be presented to the user on the display 508. Instead, a message may be presented to the user on the display 508 that an estimate of the user's CRF level will be provided after the user completes the demographic information in a user profile or performs additional workouts.

Returning to step 720, if the number of workouts is greater than the first threshold, the method moves to step 740. At step 740, a determination is made whether the total number of workouts for the user within the period of time is greater than a second threshold (e.g., five, ten, fifteen workouts, etc.). If the number of user workouts is less than the second threshold, the method moves to step 761, and the method selects a first model from the plurality of CRF models 240 for use in determining a CRF level for the user. In this case, the first model is a regression model that is uniquely configured to estimate a CRF level based only on a limited amount of workout data and without demographic data. The confidence rating associated with this model will be relatively low, and therefore a message may be displayed to the user explaining that the confidence rating of the estimated CRF level may be increased by taking further action, such as entering additional demographic data in the user profile and/or performing additional workouts. If the number of workouts is greater than the second threshold, the method moves to step 762, and the method selects a second model from the plurality of CRF models 240 for use in determining a CRF level for the user. In this case, the second model is a regression model that is uniquely configured to estimate a CRF level based only on a more complete set of workout data but still without demographic data.

Returning to step 710, if sufficient demographic data is available for the user, the method moves to step 730. At step 730, a determination is made whether the number of workouts for the user over a predetermined period of time (e.g., a month) is greater than a third threshold (e.g., zero, one, two, three workouts, etc.). If the number of workouts is not greater than the third threshold number, the method moves to step 763, and a third CRF model is selected for use in determining a CRF level of the user. This CRF model may be, for example, based exclusively on the demographic data for the user. On the other hand, if the number of workouts is greater than the third threshold in step 730, the method moves to step 750. At step 750, a determination is made whether the total number of workouts for the user within the period of time is greater than a fourth threshold (e.g., five, ten, fifteen workouts, etc.). If the number of user workouts is less than the fourth threshold, the method moves to step 764, and the method selects a fourth model from the plurality of CRF models 240 for use in determining a CRF level for the user. In this case, the fourth model is a regression model that is uniquely configured to estimate a CRF level based on complete demographic data but only a limited amount of workout data. If the number of workouts is greater than the fourth threshold in step 750, the method moves to step 765, and the method selects a fifth model from the plurality of CRF models 240 for use in determining a CRF level for the user. In this case, the fifth model is a regression model that is uniquely configured to estimate a CRF level based on a complete set of workout data and a complete set of demographic data.

It will be recognized that after selection of the appropriate CRF model, the user's CRF level is calculated based on the selected regression model. The calculated CRF level is displayed to the user on the display 508 of the user's personal electronic device 108. A confidence rating is also displayed to the user in association with the CRF level. This confidence rating may be based at least in part on the selected model. Accordingly, for each of CRF models 761-765, the associated confidence rating may be different.

Figure 8:
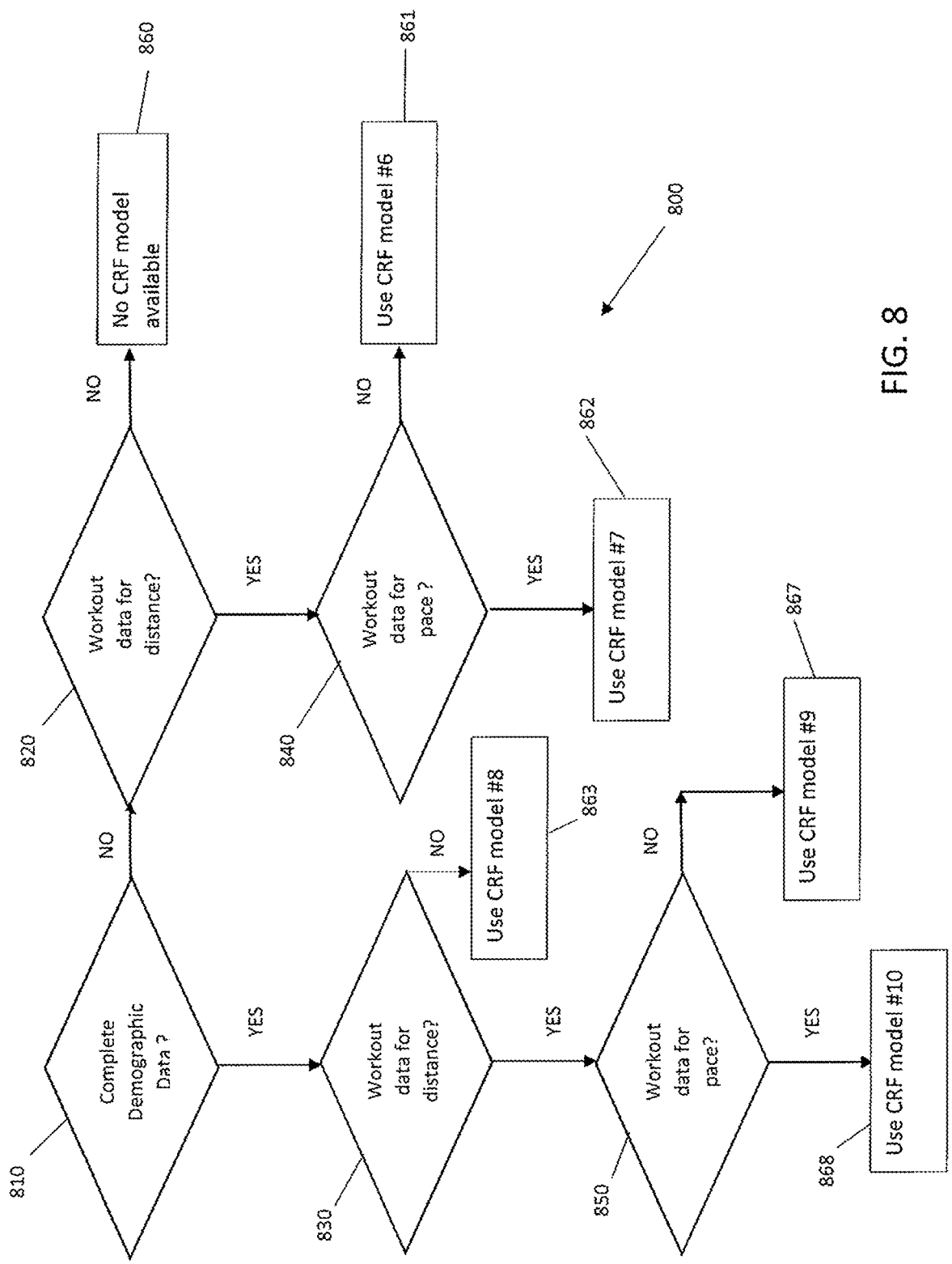
FIG. 8 is a flowchart illustrating a second method of selecting a CRF model for the method of FIG. 6.

With reference now to FIG. 8, a flowchart 800 is shown for another exemplary method for selecting a CRF model from the plurality of stored CRF models 240 (which process was referenced in block 640 of FIG. 6). It will be recognized that the method 800 of FIG. 8 is similar to the method 700 of FIG. 7, but different workout data is analyzed to determine which CRF model to use in determining a CRF level for the user. The method 800 begins with step 810 where it is determined whether the sufficient demographic data for the user is available (e.g., a determination that age, gender, height and weight all exist for the user in the database/memory 214). If sufficient demographic data is not available for the user, the method moves to step 820.

At step 820, a determination is made whether the distance traversed by the user over a predetermined period of time (e.g., a month) is greater than a first threshold (e.g., zero, one, five, ten miles, etc.). If the distance traversed by the user is not greater than the first threshold number, the method moves to step 860, and a determination is made that no CRF model is available, and no CRF level will be presented to the user on the display 508. Instead, a message may be presented to the user on the display 508 that an estimate of the user's CRF level will be provided after the user completes the demographic information in a user profile or performs additional workouts.

Returning to step 820, if the distance traversed by the user over the predetermined period of time is greater than the first threshold, the method moves to step 840. At step 840, a determination is made whether the total distance traversed by the user within the period of time is greater than a second threshold (e.g., five, twenty, fifty, one-hundred workouts, etc.). If the number of user workouts is less than the second threshold, the method moves to step 761, and the method selects a sixth model from the plurality of CRF models 240 for use in determining a CRF level for the user. In this case, the sixth model is a regression model that is uniquely configured to estimate a CRF level based only on a limited amount of workout data and without demographic data. If the number of workouts is greater than the second threshold at step 840, the method moves to step 862, and the method selects a seventh model from the plurality of CRF models 240 for use in determining a CRF level for the user. In this case, the seventh model is a regression model that is uniquely configured to estimate a CRF level based only on a more complete set of workout data but still without demographic data.

Returning to step 810, if sufficient demographic data is available for the user, the method moves to step 830. At step 830, a determination is made whether the distance traversed by the user during workouts over a predetermined period of time (e.g., a month) is greater than a third threshold (e.g., zero, one, five, ten miles, etc.). If the number of workouts is not greater than the third threshold number, the method moves to step 863, and an eighth CRF model is selected for use in determining a CRF level of the user. This CRF model may be, for example, based exclusively on the demographic data for the user. On the other hand, if the distance traversed by the user is greater than the third threshold in step 830, the method moves to step 850. At step 850, a determination is made whether the distance traversed by the user during workouts within the period of time is greater than a fourth threshold (e.g., ten, twenty, fifty miles, etc.). If the distance traversed by the user is less than the fourth threshold, the method moves to step 864, and the method selects a ninth model from the plurality of CRF models 240 for use in determining a CRF level for the user. In this case, the ninth model is a regression model that is uniquely configured to estimate a CRF level based on complete demographic data but only a limited amount of workout data. If the distance traversed by the user is greater than the fourth threshold in step 850, the method moves to step 865, and the method selects a tenth model from the plurality of CRF models 240 for use in determining a CRF level for the user. In this case, the tenth model is a regression model that is uniquely configured to estimate a CRF level based on a complete set of workout data and a complete set of demographic data.

It will be recognized that after selection of the appropriate CRF model, the user's CRF level is calculated based on the selected regression model. The calculated CRF level is displayed to the user on the display 508 of the user's personal electronic device 108. A confidence rating is also displayed to the user in association with the CRF level. This confidence rating may be based at least in part on the selected model. Accordingly, for each of CRF models 761-765, the associated confidence rating may progressively increase with the first through the fifth models.

In at least one embodiment an ensemble model approach may be utilized to arrive at an estimation of a CRF level for the users. In this approach, each of a plurality of different CRF models are applied to the available data for the user. This results in a number of different estimates of CRF levels for the user (i.e., a CRF level for each model used). After calculating the plurality of CRF levels, an average value for the plurality of CRF levels, such as a mean or median value, is used as the estimate of CRF level for the user. This method also has the benefit of providing uncertainty associated with the prediction based on the variance in the prediction model results. The ensemble method may also be implemented in a recursive manner in order to fine-tune the results for the user over time, and thereby provide an even more accurate estimation of the user's CRF level.

The fitness tracking system 100 described herein results in an improvement over past fitness tracking systems by providing multiple CRF levels to the user over time, each of which is based on a CRF model that is automatically selected by the system and then applied to the user. Different CRF models are available in the system, wherein each of the different CRF models are utilized depending upon the available user data. Furthermore, each of the CRF levels is associated with a confidence score and may include instructions to the user on how to improve the confidence score of the estimated CRF level. The detailed selection process for determining a CRF model to be used in arriving at a CRF level estimate provides significant advances over past systems that merely estimated one CRF level based on manual user inputs and/or very limited sets of data. The fitness tracking system described herein provides not only accurate CRF levels derived outside of a laboratory environment, but CRF levels that dynamically adjust as the user continues to use the fitness tracking system. With improved CRF levels and associated confidence scores, users of the fitness tracking system are provided with novel performance metrics and the ability to tailor training routines based on their known CRF level.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

It will be appreciated that the foregoing aspects of the present disclosure, or any parts or functions thereof, may be implemented using hardware, software, firmware, tangible non-transitory computer readable or computer usable storage media having instructions stored thereon, or a combination thereof, and may be implemented in one or more computer systems.

It will be apparent to those skilled in the art that various modifications and variations can be made in the disclosed embodiments of the disclosed device and associated methods without departing from the spirit or scope of the disclosure. Thus, it is intended that the present disclosure covers the modifications and variations of the embodiments disclosed above provided that the modifications and variations come within the scope of any claims and their equivalents.

What is claimed is:

1. A method of operating a fitness tracking system, the method comprising:
   receiving first activity data from at least one activity sensor carried by a user during a first number of workouts performed by the user within a period of time;
   generating first workout data from the first activity data;
   storing the first workout data in a memory, the memory further including demographic data for the user;
   selecting a first model from a plurality of models for determining a cardiorespiratory fitness (CRF) level based at least in part on the first number of workouts;
   determining a first CRF level for the user based on the selected first model;
   determining a first confidence rating for the first CRF level based at least in part on the first number of workouts;
   displaying the first CRF level and the first confidence rating on a personal electronic device associated with the user;
   receiving second activity data from the at least one activity sensor carried by the user for a second number of workouts performed by the user over the period of time;
   generating second workout data from the second activity data;
   storing the second workout data in the memory;
   selecting a second model from the plurality of models for calculating a CRF level based at least in part on the first number of workouts and the second number of workouts;
   determining a second CRF level for the user based on the selected second model, the second model configured to determining the second CRF level based at least in part on the first workout data and the second workout data;
   determining a second confidence rating for the second CRF level based at least in part on the first number of workouts and the second number of workouts; and
   displaying the second CRF level and an associated second confidence rating on the personal electronic device associated with the user.

2. The method of claim 1 wherein selecting the first model is based on the first number of workouts being less than a threshold number, wherein the first model is configured to determine the first CRF level based exclusively on the demographic data for the user in the memory.

3. The method of claim 1 wherein selecting the first model is based on the first number of workouts being greater than a threshold number, wherein the first model is configured to determine the first CRF level based exclusively on the first workout data for the user in the memory.

4. The method of claim 1 wherein selecting the second model is based a total of the first number of workouts and the second number of workouts being greater than a threshold number, wherein the second model is configured to determine the second CRF level based on the demographic data, the first workout data, and the second workout data for the user in the memory.

5. The method of claim 1 wherein the first workout data and the second workout data includes at least one of distance data and speed/pace data for each of the first number of workouts and the second number of workouts.

6. The method of claim 5 wherein selecting the first model is based at least in part on (i) the first number of workouts being greater than a threshold number, and (ii) an existence of distance data for the first number of workouts, wherein the first model determines the first CRF level based at least in part on the demographic data and the distance data for the first number of workouts.

7. The method of claim 6 wherein selecting the second model is based at least in part on (i) the first and second number of workouts being greater than a threshold number, (ii) an existence of distance data for the first and second number of workouts, and (iii) an existence of speed/pace data for each of the first and second number of workouts, wherein the second model determines the second CRF level based at least in part on the demographic data, the distance data, and the speed/pace data for the first and second number of workouts.

8. The method of claim 7 wherein the second model determines the second CRF level based at least in part on an average of the speed/pace data for the first and second number of workouts.

9. The method of claim 8 wherein the average is a mean, a median or a mode.

10. The method of claim 1 wherein each of the first number of workouts and the second number of workouts are walk workouts or run workouts.

11. The method of claim 1 wherein the first CRF level and the second CRF level are simultaneously displayed on the personal electronic devices as a time series of CRF levels.

12. The method of claim 1 wherein each of the plurality of models is associated with at least one confidence rating such that the first confidence rating is based at least in part on the selection of the first model and the second confidence rating is based at least in part on the selection of the second model.

13. The method of claim 12 wherein at least one of the plurality of models is associated with a range of confidence ratings, and wherein each confidence rating in the range of confidence ratings is associated with a number of workouts.

14. The method of claim 1 wherein the second confidence rating is based on a sensitivity analysis for a CRF level for the first and second number of workouts performed within the period of time, wherein the sensitivity analysis includes determining a variance and the confidence rating is based at least in part on the variance.

15. The method of claim 14 wherein the sensitivity analysis is a leave-one-out sensitivity analysis that calculates a plurality of CRF levels, wherein at least one of the first and second number of workouts is excluded from each of the calculated plurality of CRF levels, and wherein the variance is based on each of the calculated plurality of CRF levels.

16. A method of determining a cardiorespiratory fitness (CRF) level for a user of a fitness tracking system, the method comprising:
receiving activity data from at least one activity sensor carried by the user during a number of workouts performed by the user within a period of time;
generating workout data based on the activity data, the workout data including a plurality of workout attributes and associated values;
storing the workout data in a memory, the memory further including demographic data for the user;
when the value of a workout attribute is less than a threshold value, selecting a first CRF model, determining a first CRF level for the user using the first CRF model, and displaying the first CRF level on a personal electronic device associated with the user, wherein said workout attribute is one of time, distance traversed, speed, pace, cadence, heart rate, stride length, ground contact time, ground contact time percentage, foot strike pattern, efficiency, movement quality, fatigue index, and power output; and
when the value of the workout attribute is greater than the threshold value, selecting a second CRF model, determining a second CRF level for the user using the second CRF model, and displaying the second CRF level on the personal electronic device associated with the user, wherein the second CRF model is different from the first CRF model.

17. The method of claim 16 wherein the workout attribute is total workout distance within a period of time, wherein the determined first CRF level is based exclusively on the demographic data, and wherein the determined second CRF level is based at least in part on the workout data.

18. The method of claim 17 wherein workout data further comprises speed/pace data for each of the plurality of workouts, and wherein the determined second CRF level is based on the demographic data, the distance data, and the speed/pace data for each of a plurality of workouts.

19. A method of determining a cardiorespiratory fitness (CRF) level for a user of a fitness tracking system, the method comprising:
receiving activity data from at least one activity sensor carried by the user during a number of workouts performed by the user within a period of time;
generating workout data based on the activity data, the workout data including distance data and speed/pace data for each of the number of workouts;
storing the workout data in a memory, the memory further including demographic data for the user;
determining a CRF level for the user based on the demographic data, the distance data, and the speed/pace data;
determining a confidence rating for the CRF level, the confidence rating based at least in part on the number of workouts performed by the user within the period of time; and
displaying the CRF level and the confidence rating on a personal electronic device associated with the user, wherein the CRF level is displayed as a maximum oxygen uptake score.

20. The method of claim 19 wherein the confidence rating is based on a determination of multiple CRF levels for the number of workouts and a sensitivity analysis for the multiple CRF levels, wherein the sensitivity analysis includes determining a variance, and wherein the confidence rating is based at least in part on the variance.

* * * * *